United States Patent [19]

Grode et al.

[11] 4,267,269

[45] May 12, 1981

[54] RED CELL STORAGE SOLUTION

[75] Inventors: Gerald A. Grode, Grayslake; Jeffrey E. Miripol, Evanston, both of Ill.

[73] Assignee: Baxter Travenol Laboratories, Inc., Deerfield, Ill.

[21] Appl. No.: 118,695

[22] Filed: Feb. 5, 1980

[51] Int. Cl.$^3$ .............................................. A01N 1/02
[52] U.S. Cl. .................................................. 435/2
[58] Field of Search ........................................... 435/2

[56] References Cited

PUBLICATIONS

Ginzburg—Chem. Abst., vol. 77 (1972), p. 3320e.
Beutler et al—Chem. Abst., vol. 81 (1974), p. 61544z.
Lukasiak—Chem. Abst., vol. 79 (1973), p. 40442h.

*Primary Examiner*—Sam Rosen
*Attorney, Agent, or Firm*—Paul Flattery; John Caruso; Garrettson Ellis

[57] ABSTRACT

An aqueous red cell storage solution for packed cells which permits removal of essentially all plasma from a unit of blood, followed by reconstitution of the packed cells of the unit in preferably about 80 to 150 ml. of solution for improved cell viability on long term storage. The red cell storage solution contains adenine, glucose or fructose, sodium chloride, and mannitol.

16 Claims, No Drawings

RED CELL STORAGE SOLUTION

BACKGROUND OF THE INVENTION

Collected blood may be conventionally centrifuged to remove the plasma and the buffy coat layer, leaving behind the "packed red cells," as the mass of red cells is substantially separated from the plasma. This is desirable for several reasons, first to collect the plasma for separate therapeutic use, but also because it is desirable to administer concentrated red cells during major surgery, to provide the patient with a maximum amount of red cells with a minimum of added fluids, to avoid overburdening the patient's vascular system with excess fluids.

Accordingly, it is deemed desirable in many forms of medical practice and blood banking to store the packed red cells separately, apart from a substantial portion of the plasma, for later administration to a patient during major surgery or the like, while the collected plasma finds a separate medical use, for example administration to another patient or processing into various medical components such as antihemophilic factor, and plasma protein fraction.

In the long term storage of blood, it has been previously reported that a unit of packed red cells may be admixed with about 100 ml. of blood plasma, which is far less than normal blood, or preferably, the packed cells can be reconstituted with about 100 ml. of a solution known as SAG, comprising salt (sodium chloride) adenine, and glucose. The term "unit" of blood or packed red cells as used herein is as commonly used in blood banking circles, comprising the amount of red cells in a standard single collection of blood (typically, 225 ml. of packed cells, but of course subject to variation according to the individual donor). See for example the article by Lovric, et al., *Medical Journal of Australia* 1977, 2: 183–186.

The packed cells which are reconstituted with SAG solution have been shown to be storable for 35 days with improved viability of the red cells, when compared with packed red cells stored in a similar amount of plasma.

It has also been suggested to use mannitol, which is a type of sugar, as a reagent to improve the viability of stored blood cells. However, surprisingly, it has been found in accordance with this invention that despite the fact that SAG solution contains abundant sugar already, the addition of mannitol provides a significant improvement in the viability of packed red cells stored in contact therewith. Accordingly, longer storage times appear to be possible for packed red cells with better viability than has been previously available.

DESCRIPTION OF THE INVENTION

In accordance with this invention, an aqueous red cell storage solution is provided, particularly for admixture with highly concentrated or packed red cell, for improving the viability of the cells upon storage. The solution contains, per 100 ml., essentially from 5 to 50 mg. of adenine; from 1000 to 3500 mg. of a sugar such as glucose or fructose; from 400 to 1200 mg. of sodium chloride; and from 250 to 2000 mg. of mannitol.

Preferably, per 100 ml. of solution, from 20 to 30 mg. of adenine, from 1500 to 2500 mg. of glucose or fructose, from 500 to 1000 mg. of sodium chloride, and from 500 to 1500 mg. of mannitol are present. Particularly, from 700 to 800 mg. of mannitol may be present per 100 ml. of solution, for example, 750 mg.

A specifically preferred solution in accordance with this invention may contain, per 100 ml., about 27 mg. of adenine, 2000 mg. of glucose, 900 mg. of sodium chloride and 750 mg. of mannitol, these solutes being carefully dissolved in distilled water and then sterilized and sealed in conventional manner.

For example, a conventional triple or quadruple pack blood bag of conventional design for receiving one unit of blood, comprising a donor bag and two or three satellite transfer bags or packs may be utilized, with typically about 60 to 200, and preferably 80 to 150 ml., of the above specifically described solution being placed in one of the transfer bags. Preferably an extra interior seal, openable from the exterior, is provided to the connecting tube between the solution-containing transfer bag and the donor bag adjacent the transfer bag, for example, the CELL-PROOF ® closure of the Fenwal Division of Baxter Travenol Laboratories, or the closure of U.S. Pat. No. 4,181,140.

A unit of blood may be accordingly collected in conventional manner into the donor bag. The three or four bag system may be conventionally centifuged, and the plasma and buffy coat layer can be expressed into an empty transfer bag by appropriate manipulation of the clamping and internal sealing system provided by the bag system. The red cell storage solution in the first transfer pack may then be expressed into the donor bag, and the donor bag may then be sealed and separated from the remaining bags for long term storage.

Following this, the plasma-containing transfer bag may be centrifuged to separate platelets, with the platelet-poor plasma then being expressed from the plasma-containing transfer bag into the transfer pack which formerly contained red cell storage solution in the case of a triple bag. The transfer packs may be then separated for separate storage and therapeutic administration or other use as desired. The fourth bag of a multiple bag unit may be provided to receive the leucocytes, for example.

Long-term storage of packed red cells at 4° C. under conventional storage conditions for 35 days and more is possible, with the red cells exhibiting improved viability in accordance with this invention.

Preferably, the donor bag contains a usual amount of CPD preservative. Also, the solution of this invention may contain other ingredients as desired, for example, guanosine, or phosphate, calcium, magnesium or potassium ion, etc.

The following example is offered for illustrative purposes only, and is not intended to limit the invention of this application, which is as defined in the claims below.

Example. A triple bag system of the conventional design of the Fenwal BLOOD-PACK ® system, containing a donor bag with CPD preservative of the usual type, and two transfer bags were utilized in this experiment, but also containing an added inner seal at the first transfer bag, openable from the exterior, in the tube leading between the donor bag and the transfer bag. Where indicated, the first transfer bag contained 100 ml. of the cell diluent solution described below. In each experiment a unit of blood was collected in the donor bag, centrifuged, and the plasma was expressed from the donor bag to the second transfer bag. Then, the 100 ml. of solution in the first transfer bag was expressed into the donor pack, which was then sealed, separated from the bag system, and stored for 35 days at 4° C. in conventional manner.

Referring to experiments (a) through (e) as described below, in experiment (a), the 100 ml. of solution in the first transfer bag was simply saline solution containing 900 mg. of sodium chloride per 100 ml.

In experiment (b), no diluent solution at all was used, with the packed cells being stored in their undiluted configuration.

In experiment (c), the packed cells were diluted with 100 ml. of plasma, which was simply re-expressed back to the cells from the second transfer bag containing the plasma.

In experiment (d) below, the 100 ml. of solution placed in the transfer pack contained 1000 mg. of glucose, approximately 17 mg. of adenine, and about 800 mg. of sodium chloride. No mannitol was present.

In experiment (e) below, the 100 ml. of solution in the first transfer pack was an embodiment of the solution of this invention, containing 27 mg. of adenine; 2000 mg. of glucose; approximately 500 mg. of sodium chloride; and 750 mg. of mannitol.

After processing of the blood in accordance with the technique described above, each of the donor bags of the five experiments (a) through (e) were stored at 4° C. for 35 days.

At the conclusion of the 35 days, the plasma hemoglobin was measured in terms of mg. per 100 ml., and the red cell ATP was measured and expressed in Table I below as micromoles per gram of red cell hemoglobin. T,0070

Accordingly, it can be seen that in accordance with this invention, substantially decreased plasma hemoglobin levels, and significantly increased ATP levels are achieved on 35 day storage of packed cells, when compared with prior art techniques.

That which is claimed is:

1. An aqueous cell storage solution which contains per 100 ml. of solution essentially from 5 to 50 mg. of adenine; from 1000 to 3500 mg. of a sugar selected from the group consisting of glucose and fructose; from 400 to 1200 mg. of sodium chloride; and from 250 to 2000 mg. of mannitol.

2. The solution of claim 1 which contains, per 100 ml. of solution, from 20 to 30 mg. of adenine.

3. The solution of claim 1 which contains, per 100 ml. of solution, from 1500 to 2500 milligrams of said sugar.

4. The solution of claim 3 in which said sugar is glucose.

5. The solution of claim 1 which contains, per 100 ml. of solution, from 500 to 1000 mg. of sodium chloride.

6. The solution of claim 1 which contains, per 100 ml. of solution, from 500 to 1500 mg. of mannitol.

7. The solution of claim 6 which contains, per 100 ml. of solution, from 700 to 800 mg. of mannitol.

8. An aqueous red cell storage solution which contains, per 100 ml. of solution, essentially from 20 to 30 mg. of adenine; from 1500 to 2500 mg. of a sugar selected from the group consisting of glucose and fructose; from 500 to 1000 mg. of sodium chloride; and from 250 to 2000 mg. of mannitol.

9. The solution of claim 8 in which said sugar is glucose.

10. The solution of claim 9 in which from 700 to 800 mg. of mannitol are present per 100 ml. of solution.

11. A unit of red blood cells, intermixed with from 60 to 200 ml. of an aqueous red cell storage solution which contains, per 100 ml. of said storage solution, essentially from 5 to 50 mg. of adenine; from 1000 to 3500 mg. of a sugar selected from the group consisting of glucose and fructose; from 400 to 1200 mg. of sodium chloride, and from 250 to 2000 mg. of mannitol.

12. The unit of packed blood cells and mixed solution of claim 11 in which CPD preservative is present.

13. A unit of packed red blood cells, mixed with from 80 to 150 ml. of an aqueous red cell storage solution which contains, per 100 ml. of solution, essentially from 20 to 30 mg. of adenine; from 1500 to 2500 mg. of a sugar selected from the group consisting of glucose and fructose; from 500 to 1000 mg. of sodium chloride; and from 500 to 1500 mg. of mannitol.

14. The unit of packed blood cells and mixed solution of claim 13 in which said sugar is glucose.

15. The unit of packed blood cells and mixed solution of claim 14 in which from 700 to 800 mg. of mannitol is present per 100 ml. of said solution.

16. The unit of packed blood cells and mixed solution of claim 13 in which CPD blood preservative is present.

* * * * *

UNITED STATES PATENT AND TRADEMARK OFFICE
CERTIFICATE OF CORRECTION

PATENT NO. : 4,267,269

DATED : May 12, 1981

INVENTOR(S) : Gerald A. Grode, et al

It is certified that error appears in the above—identified patent and that said Letters Patent is hereby corrected as shown below:

Column 3, line 33, insert Table 1 as per the attached sheet.

Patent No. 4,267,269

TABLE I

| TREATMENT CONDITIONS PRIOR TO STORAGE | PLASMA HEMOGLOBIN (mg./100ml.) | ATP (Micromoles/g. Red Cell Hemoglobin) |
|---|---|---|
| (a) packed cells with saline solution | more than 1000 | about 1.5 |
| (b) packed cells only | more than 1000 | about 2.5 |
| (c) packed cells plus 100 ml. plasma | 200 | about 1.75 |
| (d) saline, adenine, glucose solution without mannitol | 500 | about 4 |
| (e) the solution of this invention containing mannitol | 180 | about 5 |

Signed and Sealed this

*Twenty-third* Day of *March 1982*

[SEAL]

Attest:

GERALD J. MOSSINGHOFF

Attesting Officer  *Commissioner of Patents and Trademarks*